US012788585B2

(12) United States Patent
Entis, Sr.

(10) Patent No.: US 12,788,585 B2
(45) Date of Patent: Nov. 10, 2026

(54) JOINT REPLACEMENT APPARATUS

(71) Applicant: Allan Cecil Entis, Sr., Tel Aviv (IL)

(72) Inventor: Allan Cecil Entis, Sr., Tel Aviv (IL)

(73) Assignee: Allan Cecil Entis, Tel Aviv (IL)

( * ) Notice: Subject to any disclaimer, the term of this patent is extended or adjusted under 35 U.S.C. 154(b) by 1032 days.

(21) Appl. No.: 17/794,967

(22) PCT Filed: Jan. 24, 2021

(86) PCT No.: PCT/IL2021/050070
§ 371 (c)(1),
(2) Date: Jul. 24, 2022

(87) PCT Pub. No.: WO2021/149057
PCT Pub. Date: Jul. 29, 2021

(65) Prior Publication Data

US 2023/0101142 A1 Mar. 30, 2023

Related U.S. Application Data

(60) Provisional application No. 62/964,666, filed on Jan. 23, 2020, provisional application No. 62/986,813,
(Continued)

(51) Int. Cl.

| | |
|---|---|
| ***A61F 2/46*** | (2006.01) |
| ***A61B 17/92*** | (2006.01) |

(Continued)

(52) U.S. Cl.
CPC .......... *A61F 2/4603* (2013.01); *A61B 17/921* (2013.01); *A61F 2/4607* (2013.01); *A61B 2017/00402* (2013.01); *A61B 34/30* (2016.02); *A61F 2002/4619* (2013.01); *A61F 2002/4683* (2013.01)

(58) Field of Classification Search
CPC ........... A61F 2/4607; A61F 2002/4681; A61B 17/74; A61B 17/92; A61B 34/30
See application file for complete search history.

(56) References Cited

U.S. PATENT DOCUMENTS

| | | | | |
|---|---|---|---|---|
| 5,019,083 A * | 5/1991 | Klapper | ................ | A61F 2/4607 606/86 R |
| 7,001,393 B2 * | 2/2006 | Schwenke | ............. | A61F 2/4618 606/86 R |

(Continued)

FOREIGN PATENT DOCUMENTS

| | | |
|---|---|---|
| CN | 105250054 | 1/2016 |
| DE | 19852138 | 5/2000 |

(Continued)

OTHER PUBLICATIONS

Office Action dated Aug. 17, 2023 for European Application No. 21708765.9 filed Aug. 22, 2022.

(Continued)

*Primary Examiner* — David W Bates
(74) *Attorney, Agent, or Firm* — A.C. Entis-IP Ltd; Allan C. Entis

(57) ABSTRACT

Apparatus (20) for performing a joint replacement procedure comprising: a vibrator (50) configured to be coupled to a stem (120) and be excited stem out from the canal.

21 Claims, 12 Drawing Sheets

Related U.S. Application Data filed on Mar. 9, 2020, provisional application No. 63/046,728, filed on Jul. 1, 2020, provisional application No. 63/106,372, filed on Oct. 28, 2020.

(51) Int. Cl.

| | |
|---|---|
| ***A61B 34/30*** | (2016.01) |
| *A61B 17/00* | (2006.01) |

(56) References Cited

U.S. PATENT DOCUMENTS

| | | | | |
|---|---|---|---|---|
| 7,189,241 | B2 * | 3/2007 | Yoon | A61B 17/1659 606/85 |
| 7,879,043 | B2 * | 2/2011 | Meneghini | A61F 2/4607 600/587 |
| 8,167,823 | B2 * | 5/2012 | Nycz | A61F 2/4609 600/595 |
| 8,393,409 | B2 * | 3/2013 | Pedicini | B25D 11/125 173/132 |
| 10,076,349 | B2 * | 9/2018 | Voic | A61B 17/320068 |
| 10,149,711 | B2 * | 12/2018 | Bittenson | A61B 17/92 |
| 10,245,160 | B2 * | 4/2019 | Behzadi | A61F 2/3609 |
| 10,806,529 | B2 * | 10/2020 | Timperley | A61B 17/8808 |
| 2002/0183851 | A1 * | 12/2002 | Spiegelberg | A61F 2/4607 606/92 |
| 2003/0125620 | A1 * | 7/2003 | Satou | B06B 3/00 600/437 |
| 2006/0015119 | A1 | 1/2006 | Plassky et al. | |
| 2010/0100139 | A1 | 4/2010 | Young | |
| 2014/0277028 | A1 * | 9/2014 | Voic | A61B 17/320068 606/169 |
| 2016/0206445 | A1 * | 7/2016 | Gheevarughese | A61F 2/36 |
| 2016/0338751 | A1 * | 11/2016 | Kellar | A61B 17/921 |
| 2017/0080166 | A1 * | 3/2017 | Bagwell | A61B 17/3423 |
| 2018/0078201 | A1 * | 3/2018 | Behzadi | A61B 5/11 |
| 2019/0350726 | A1 * | 11/2019 | Behzadi | A61F 2/4657 |

FOREIGN PATENT DOCUMENTS

| | | |
|---|---|---|
| FR | 2783702 | 3/2000 |
| JP | S6045356 | 3/1985 |
| WO | 02074195 | 9/2002 |
| WO | 2017123506 | 7/2017 |

OTHER PUBLICATIONS

International Search Report and Written Opinion dated Jul. 16, 2021 for PCT/IL2021/050070.

* cited by examiner

JOINT REPLACEMENT APPARATUS

RELATED APPLICATIONS

The present application is a US National Phase of PCT Application No. PCT/IL2021/050070, filed on Jan. 24, 2021 which claims the benefit under 35 U.S.C. 119 (e) of U.S. Provisional Application 62/964,666 filed on Jan. 23, 2020, U.S. Provisional Application 62/986,813 filed on Mar. 9, 2020, U.S. Provisional application 63/046,728 filed on Jul. 1, 2020 and U.S. Provisional application 63/106,372 filed on Oct. 28, 2020 the disclosures, of which are incorporated herein by reference.

FIELD

Embodiments of the disclosure relate to providing apparatus and methods to perform joint replacement surgery such as hip or knee joint replacement surgery.

BACKGROUND

The human hip joint is a ball and socket joint with the ball the rounded head of the femur and the socket a matching recess formed in the pelvis. Replacing a hip joint typically involves replacing the native ball with a prosthetic ball and fitting the pelvis with a prosthetic socket, also referred to as an acetabular cup, that matches the prosthetic ball. The ball is replaced by sawing off the head of the femur to expose the femoral canal, reaming out the femoral canal with a series of broaches of increasing size, and press fitting into the femoral canal an elongate metallic stem, having a neck to which the prosthetic ball is mounted. The broaches and femoral stem are introduced into and fit to the femoral canal by tapping with a mallet and/or impactor. A surgeon performing the hip replacement surgery determines when the broaches and femoral stem are properly introduced into the femoral canal by "feel" and listening to the sounds made by the tapping.

SUMMARY

An aspect of an embodiment of the disclosure relates to providing apparatus hereinafter also referred to as a STEM-FIT apparatus, system, or simply STEM-FIT, for performing hip replacement surgery on a patient. The apparatus generates vibrations in and applies force to a broach or stem that cooperate to insert and fit the broach or stem to the femoral canal of the patient's leg being operated on to replace a damaged hip joint. Hereinafter for convenience of presentation, unless otherwise indicated or evident from context, a broach, and a stem intended to remain permanently inserted into the femoral canal at the conclusion of the hip replacement surgery are generically referred to as a stem.

In an embodiment STEM-FIT comprises a stem vibrator that may be excited to generate vibrations of the stem, and a driver configured to apply force that cooperates with the vibrations to insert the stem into or extract the stem out from the femoral canal with the vibrations to insert the stem into or extract the stem out from the femoral canal of the femur being operated on. Force delivered by the driver may be a continuous force and/or an impulse force. An impulse force is a force delivered over a short period of time such as a force delivered to a stem by an impactor striking the stem during a conventional hip replacement operation. A continuous force is a non-impact force. In an embodiment Stem-Fit vibrates the stem during application of force to the stem. Optionally, STEM-FIT vibrates the stem at a frequency so that during the application of force the stem undergoes a plurality of vibration cycles Optionally, Stem-Fit vibrates the stem during a period of time when the driver does not apply force to the stem. Stem-Fit may apply force to a stem without vibrating the stem.

Optionally, STEM-FIT comprises a torquing system operable to rotate the stem to a desired azimuthal angle about a longitudinal axis of the stem. In an embodiment the torquing system comprises at least one piezoelectric vibrator, hereinafter referred to as a torquing vibrator, and a torque transmission that couples vibrations of the torquing vibrator to apply a torque that rotates the stem. In an embodiment, STEM-Fit comprises an attitude control system operable to control a direction along which the longitudinal axis of the stem points during insertion and/or extraction of the stem from the femoral canal. Optionally, the attitude control system comprises a global attitude transmission comprising an inner spherical surface rotatably nested in an outer spherical surface coupled to the stem. The inner surface, also referred to as a "rotor", is optionally rotatable by at least one piezoelectric vibrator that couples the inner surface to the outer surface, also referred to as a stator.

STEM-FIT optionally comprises a controller that controls the frequency and amplitude of the stem vibrator vibrations and force applied by the driver to the stem to control rate and depth of insertion of the stem into the canal and/or a rate of extraction of the stem out from the canal. The controller may operate to control the torquing system to rotate the stem about the stem longitudinal axis to an azimuthal angle advantageous for matching a prosthetic femoral head that seats on the stem to an acetabular cup mounted in the pelvis to receive the femoral head. In an embodiment the controller may operate to control the attitude system to point the longitudinal axis of the stem in a polar angle advantageous for matching the prosthetic femoral head to the acetabular cup.

Optionally, to provide accurate insertion, rotation and/or pointing of the stem, the controller controls vibrations generated by the stem vibrator to be out of phase with vibrations generated by the torquing system and/or to be out of phase with vibrations generated by the global attitude system, and/or vibrations generated by the torquing system to be out pf phase with vibrations generated by the global attitude system. Optionally a phase difference of out of phase vibrations is equal to about 180°.

In an embodiment STEM-FIT comprises at least one sensor that generates and transmits sensor signals to the controller responsive to amplitudes and frequencies of vibrations excited in the stem by vibrations of the stem vibrator. The controller may process the received sensor signals to determine characteristics of a frequency spectrum of vibrations generated in the stem by vibrations of the stem vibrator. In an embodiment the controller controls the stem vibrator and driver responsive to the determined characteristics of the frequency spectrum. Optionally, the controller controls the torquing vibrator responsive to the determined characteristics of the frequency spectrum.

In an embodiment, the controller excites the stem vibrator to vibrate during excitation periods interspersed by passive periods during which the controller does not excite the stem vibrator to vibrate. During passive periods, the controller receives and processes sensor signals from the at least one sensor to determine amplitudes, intensities, frequencies and/or decay time constants of vibrations excited in the stem during preceding excitation periods. The controller controls the stem vibrator and/or driver responsive to the determined amplitudes, intensities, frequencies, and/or decay times.

Optionally, the controller processes sensor signals to determine resonant frequencies of the system of stem coupled to femoral bone. The controller may control the stem vibrator and driver responsive to the resonant frequencies or characteristics of the resonant frequencies. For example, the controller may process the sensor signals to determine and track changes in resonant or natural frequencies of the stem-bone system during insertion of a stem into the femur. The controller may control vibrations of the stem vibrator to track changes in the resonant frequencies and optionally vibrate at an offset frequency different from a tracked resonant frequency in order to maximize relative displacement of the surface of the stem and bone tissue in the femoral canal. In an embodiment the controller may control vibrations of the stem vibrator to vibrate substantially at a resonant frequency of the stem-bone system tracked by the controller.

In an embodiment the controller controls the stem vibrator to transmit an acoustic pulse into the femur. The controller may process sensor signals from the at least one sensor to determine propagation velocity of the acoustic pulse, or velocities of components of the acoustic pulse in the femur bone and control the stem vibrator and/or driver responsive to the determined velocity or velocities. In an embodiment the controller may process sensor signals to determine attenuation of the acoustic pulse in propagating along and/or out from the femur. The controller may control the stem vibrator and/or driver responsive to the determined attenuation.

In an embodiment the stem vibrator comprises at least one piezoelectric vibrator that operates as a stem vibrator to excite vibrations of the stem during excitation periods and optionally as a sensor of the at least one sensor during passive periods. The driver may comprise a hydraulic, pneumatic, or magnetic piston for generating force applied to the stem. Optionally, the driver comprises a push cable and actuator controllable to push the push cable to apply force to the stem.

In an embodiment the controller comprises a processor having computer executable instructions which the processor executes to process sensor signals. Optionally, the processor comprises instructions for implementing any of various regression algorithms and/or classifiers, such as rule based classifiers, clustering algorithms and/or artificial intelligence (AI) for processing sensor signals to determine how to control the stem vibrator, torquing system, global attitude system, and/or driver, and to determine when to stop applying force and/or torque to insert a stem into a femoral canal, and when a stem is properly fit into a femoral canal.

The controller, driver, stem vibrator, and/or torquing system may be comprised in, or configured as a robot operable to autonomously or semi-autonomously perform a hip replacement operation.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which the embodiment is intended. Unless otherwise indicated, the word "or" in the description and claims is considered to be the inclusive "or" rather than the exclusive or, and indicates at least one of, or any combination of items it conjoins.

This summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

Figure 1:
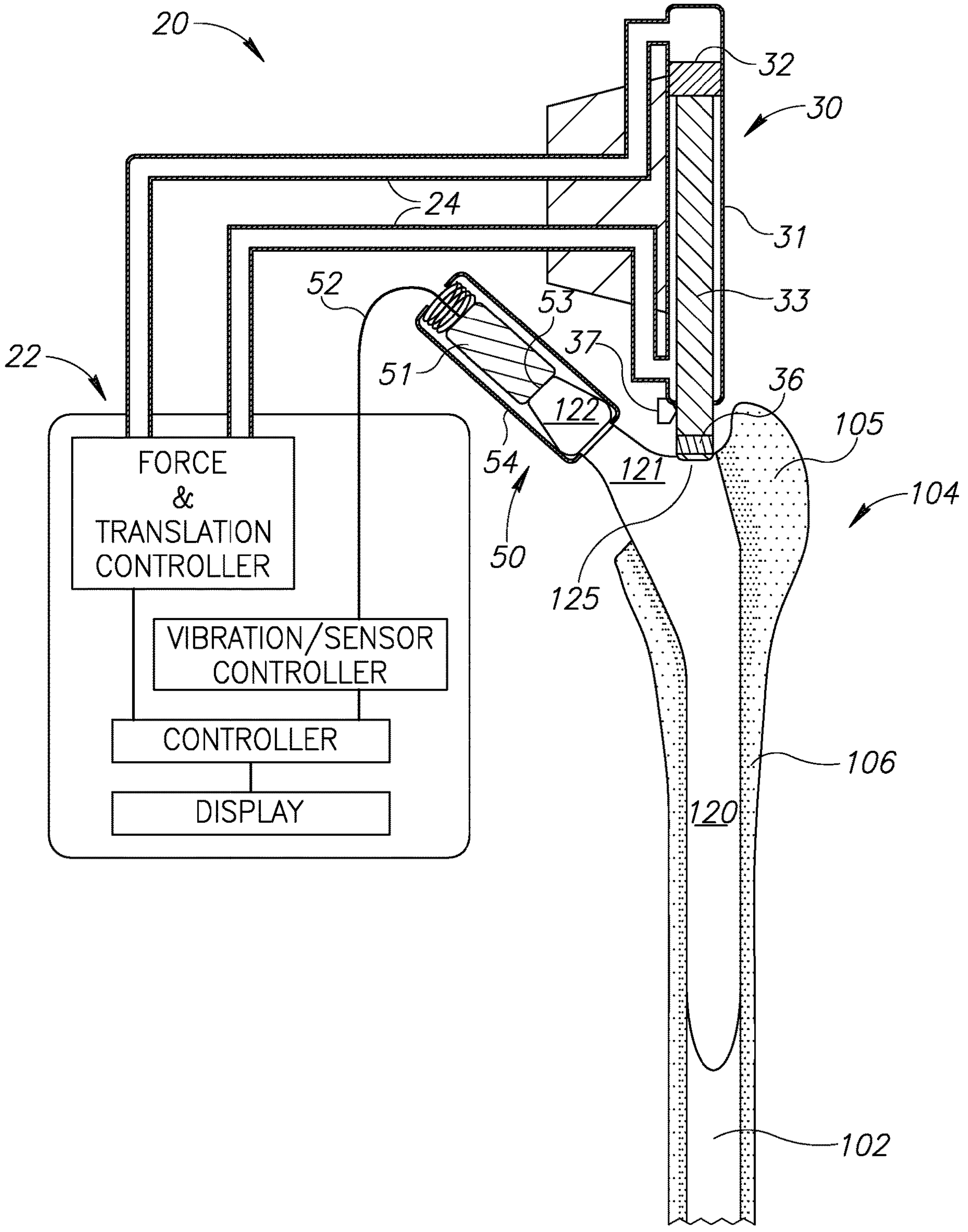
FIG. 1 schematically shows a STEM-FIT comprising a piezoelectric stem vibrator and a hydraulic cylinder controlled by a controller to insert a prosthetic stem into a femoral canal, in accordance with an embodiment of the disclosure.

FIG. 1 schematically shows a STEM-FIT 20 operating to insert a stem 120 into a femoral canal 102 of a person's femur 104 during a hip replacement procedure in accordance with an embodiment of the disclosure. STEM-FIT 20 optionally comprises a driver 30 having a pneumatic or hydraulic cylinder 31, a stem vibrator 50, optionally comprising a piezoelectric stem vibrator 51, and a controller 22 that controls driver 30 and stem vibrator 50. At least one control and sense wire 52 connects piezoelectric stem vibrator 51 to controller 22, and fluid flow lines 24 connect cylinder 31 to the controller. The controller controls the stem vibrator and driver, optionally substantially simultaneously, to generate vibrations in stem 120 and apply force to the stem that cooperate to drive the stem into femoral canal 102 until the stem is securely lodged in the canal, optionally with trabecular bone 105, schematically represented by speckled areas of femur 104 compressed and the stem in contact or near contact with cortical bone 106 of the femur.

Piezoelectric stem vibrator 51 is optionally coupled to a neck 121 of stem 120 by an adapter 54 that grips a head 122 of the neck and spring loads the piezoelectric stem vibrator to resiliently press a contact surface 53 of the piezoelectric stem vibrator to the neck head 122. Controller 22 may apply voltage to piezoelectric stem vibrator 51 via control and sense wire 52 to excite the stem vibrator to vibrate and generate vibrations in stem 120 having desired frequencies and amplitudes. Excited vibrations may be any longitudinal and/or transverse vibrations suitable for use in combination with force applied by driver 30 to aid in inserting stem 120 into canal 102. Longitudinal vibrations are vibration parallel to the length of stem 120. Transverse vibrations are vibrations that are perpendicular to the length of the stem. The vibrations may by way of example, operate to ablate and/or compress trabecular bone 105 in the canal to aid the force in introducing and coupling stem 120 to cortical bone 106 of the femur. Optionally, the vibrations are ultrasonic vibrations. Optionally, piezoelectric stem vibrator 51 may be operated by controller 22 as a sensor that generates voltages transmitted over at least one control and sense wire 52 to the controller responsive to vibrations of stem 120.

By way of example of operation of driver 30, controller 22 may excite piezoelectric stem vibrator 51 to vibrate and generate longitudinal and/or transverse vibrations in stem 120 for a first, limited duration excitation period. During a subsequent passive, "sensor" period, controller 22 may receive a time dependent analog voltage waveform that the piezoelectric stem vibrator generates responsive to vibrations that the piezoelectric stem vibrator generated during the preceding excitation period. In an embodiment, controller 22 processes the received voltage waveform to determine an, optionally power, frequency spectrum for the vibrations, and decay of frequency components of the spectrum. Optionally, processing comprises sampling the received waveform to generate a discrete time sequence of voltage samples and transforming the samples in accordance with an integral transform to generate a discrete transform. In an embodiment the controller uses the transform to determine time dependent characteristics of the frequency spectrum. Characteristics of the frequency spectrum and decay times of the spectrum frequencies may be used to indicate how strongly stem 120 is coupled to cortical and trabecular bone and/or a depth to which stem 120 is inserted into femoral canal 102. In an embodiment, the controller uses a classifier to process the transform to determine a state of coupling of the stem to femoral bone.

Cylinder 31 comprises a piston 32, and a piston rod 33 configured to be coupled to, optionally, a shoulder region 125 of stem 120. Cylinder 31 may be held in position by a mechanical structure (not shown) mounted or coupled to an operating table (not shown) on which a patient undergoing hip replacement is supported. By way of example, the mechanical structure may comprise an articulated arm (not shown) configured to grip piston 31 and be adjusted and clamped to stabilize the piston in a desired location and attitude. Piston rod 33 may be formed having a threaded end (not shown in FIG. 1) that is screwed into a matching threaded hole (not shown) in stem 120 to couple the piston rod to stem 120.

Controller 22 controls force that piston rod 33 applies to stem 120 and movement of piston rod 33 to move stem 120 into or out from femoral canal 102 by controlling pressure, direction and amount of fluid pumped to or from cylinder 31 through fluid flow lines 24. Optionally, piston rod 33 comprises an, optionally piezoelectric, force sensor 36 that generates force signals responsive to magnitude of force that the piston rod applies to stem 120. Optionally, driver 30 comprises at least one position sensor 37 that generates position signals responsive to travel of piston rod 33.

In an embodiment, controller 22 controls travel of piston rod 33 and force that the piston rod applies to stem 120 based on signals from position sensor 37, force sensor 36, and/or characteristics of a frequency spectrum of vibrations that piezoelectric stem vibrator 51 generates in stem 120. For example, it is expected that when stem 120 is firmly pressed into femoral canal 102, trabecular bone 105 in the canal will be substantially compressed or removed and the stem in close and/or intimate contact with cortical bone 106 of the femur. As a result, the frequency spectrum may exhibit enhanced characteristics associated with a length of the canal, thickness, density and/or elasticity of cortical bone. Controller 22 may therefore quench vibrations of stem vibrator 51 and control driver 30 to terminate application of force to stem 120 when enhancement of the associated frequency spectrum characteristics is exhibited by the frequency spectrum.

Figure 2:
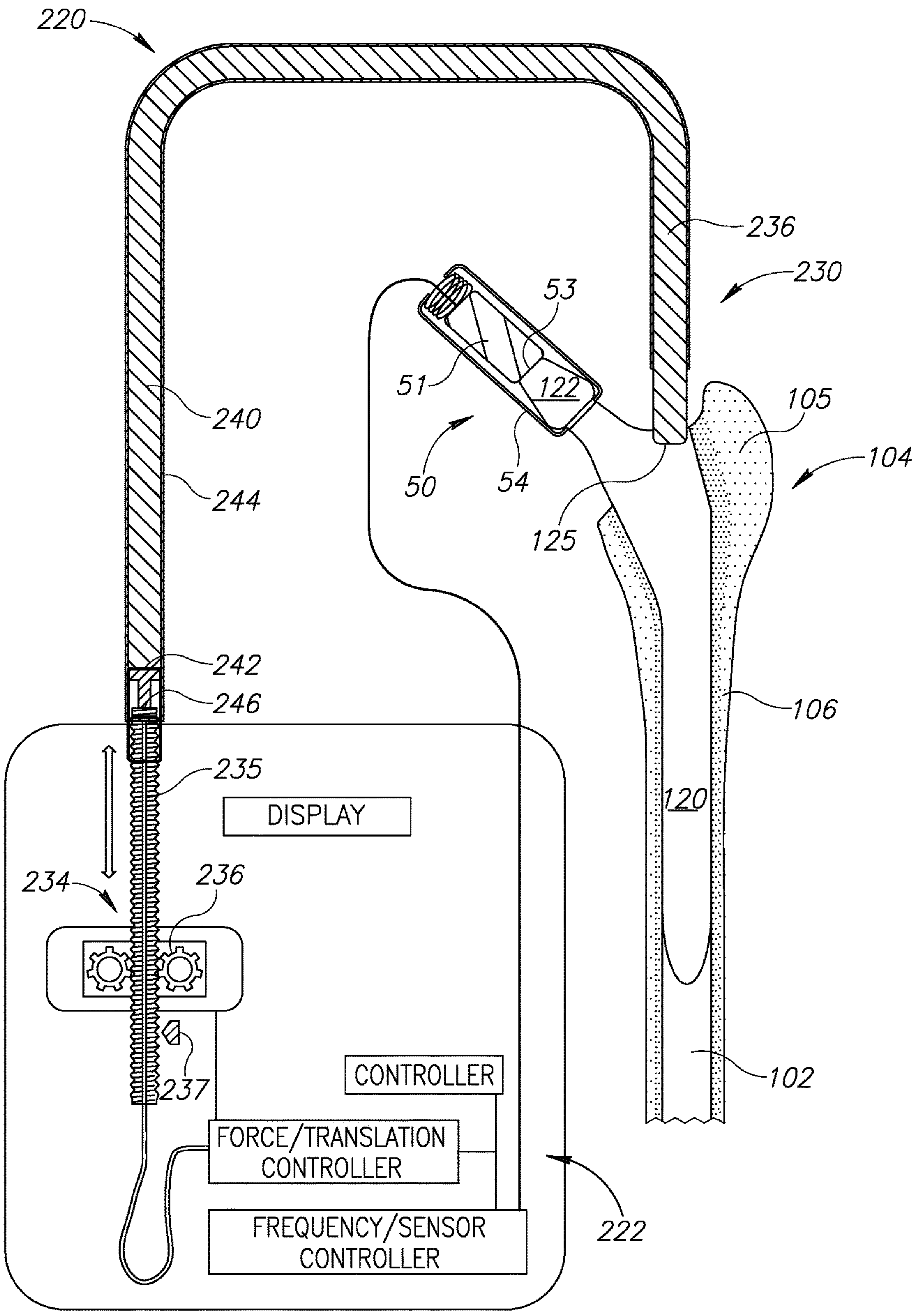
FIG. 2 schematically shows a STEM-FIT comprising a piezoelectric stem vibrator and a push rod controlled by a controller to insert a prosthetic stem into a femoral canal, in accordance with an embodiment of the disclosure.

FIG. 2 schematically shows a STEM-FIT 220, optionally comprising a driver 230 having a rack and pinion transmission 234 coupled to a push rod 240 for applying force and inserting stem 120 into femoral canal 102, and a controller 222, in accordance with an embodiment of the disclosure. Rack and pinion transmission 234 optionally comprises a rack 235 and pinions 236. Push rod 240 is coupled to rack 235 by an adapter 242 and is housed in a guide tube 244 in which the push rod may be translated. An optionally piezoelectric force sensor 246 sandwiched between push rod 240 and rack 235 transmits force signals to controller 222 responsive to force that push rod applies to stem 120. Optionally, rack and pinion 234 comprises a position sensor 237 that generates position signals responsive to translation of rack 235 and thereby push rod 240 and stem 120. In an embodiment controller 222 controls rack and pinion 234 and/or piezoelectric stem vibrator 51 responsive to the force and/or position signals, and/or characteristics of a frequency spectrum of vibrations that piezoelectric stem vibrator generates in stem 120.

Figure 3:
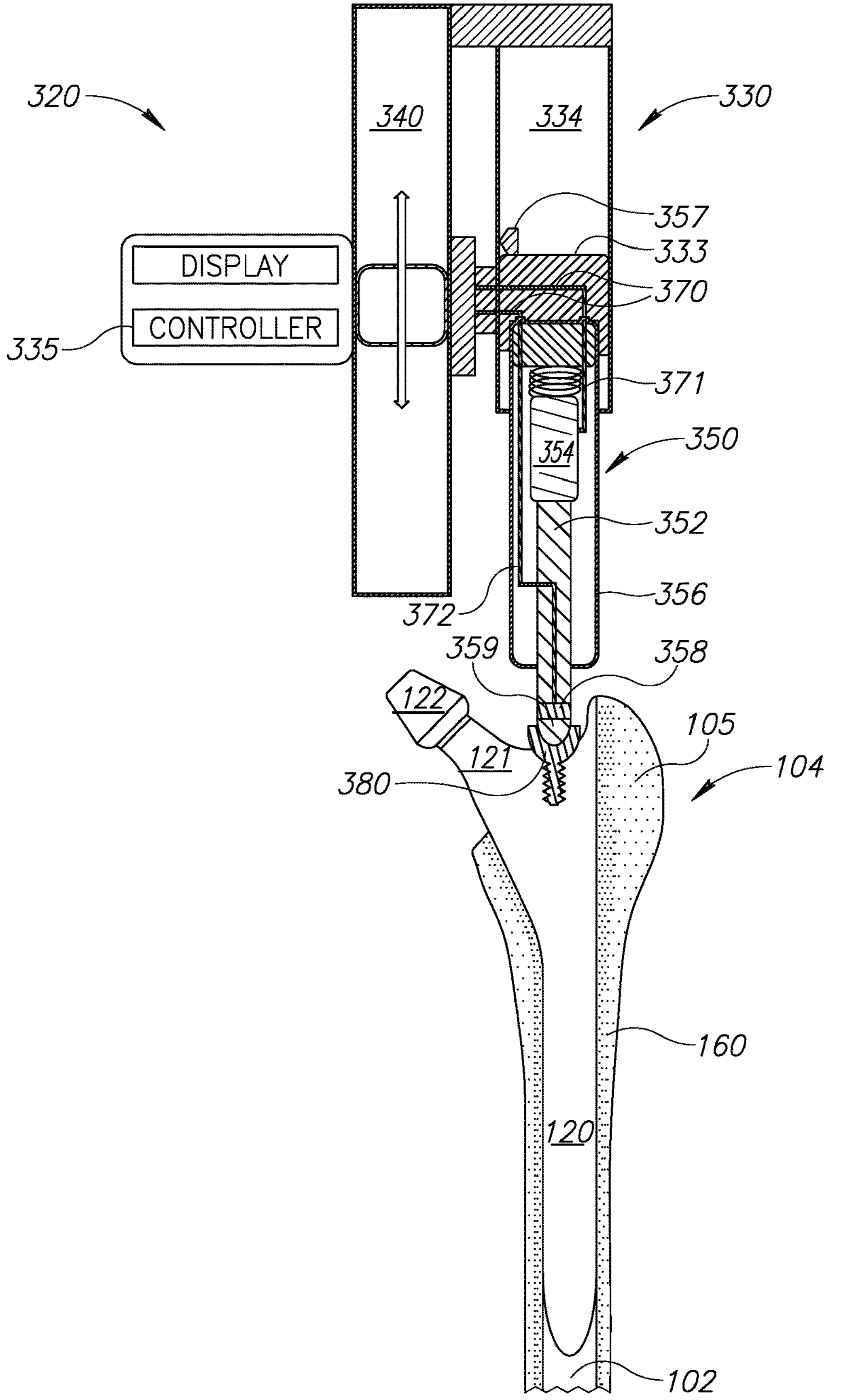
FIG. 3 schematically shows a STEM-FIT having a stem vibrator and push rod connected in series with and operated by a rodless cylinder and controller to insert a prosthetic stem into a femoral canal, in accordance with an embodiment of the disclosure.

FIG. 3 schematically shows a STEM-FIT 320 having a driver 330 optionally comprising a throwaway pusher tool 350 removably mounted to a carriage 333 housed in a guide tube 334 and driven by a rodless cylinder 340 that is controlled by a controller 335, in accordance with an embodiment of the disclosure. Pusher tool 350 optionally comprises a push rod 352 mounted to, an optionally piezoelectric, stem vibrator 354 housed in a housing 356. Driver 330 optionally comprises a position sensor 357 that generate position signals responsive to motion of carriage 333 and thereby translation of push rod 352. Push rod 352 optionally comprises a force sensor 358 that generates force signals responsive to force that an end 359 of the push rod applies to stem 120. Optionally, as shown in FIG. 3, end 359 of push rod 352 is configured to seat in an adapter socket 380 which is optionally screwed into stem 120. Housing 356 is optionally a pluggable housing that may be plugged into carriage 333 to mechanically mount the pusher tool to carriage 333 and electrically connect the pusher tool to at least one, and as shown in FIG. 3 optionally two, control and/or signal wires 370 in the carriage which connect the pusher tool to controller 335. When plugged into carriage 333 at least one control and signal wire 371 coupled to piezoelectric stem vibrator 354 and a signal wire 372 connected to force sensor 358 are coupled to signal and control wires in carriage 333 and thereby to controller 335.

Figure 4:
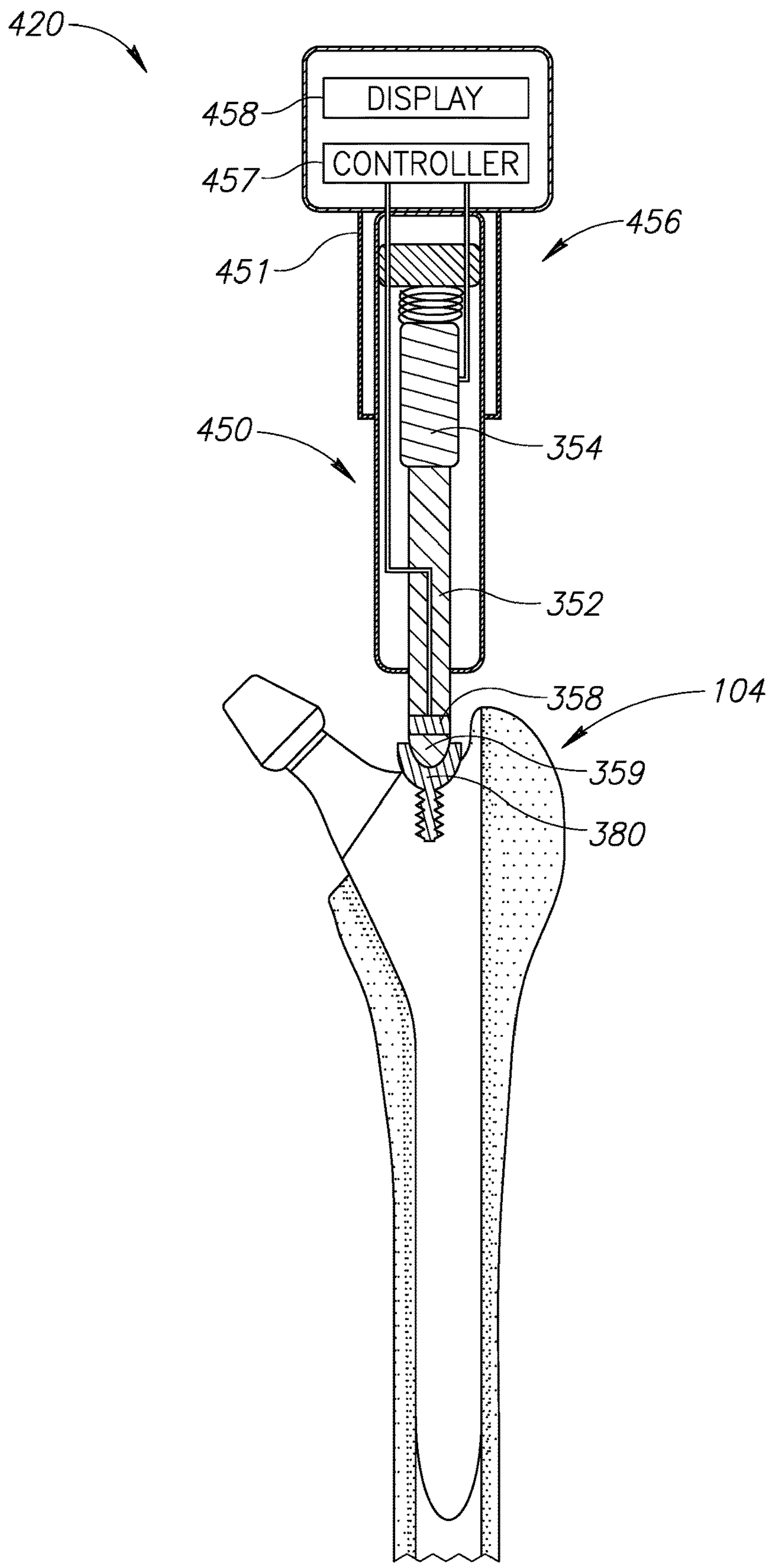
FIG. 4 schematically shows a hand operated STEM-FIT comprising a piezoelectric stem vibrator being operated to insert a prosthetic stem into a femoral canal, in accordance with an embodiment of the disclosure.

FIG. 4 schematically shows a manually operated STEM-FIT 420 optionally comprising a pusher tool 450 removably plugged into a socket 451 of a handheld housing 456 optionally comprising a controller 457 and display 458, in accordance with an embodiment of the disclosure. Pusher tool 450 is similar to pusher tool 350. STEM-FIT 420 is hand-pressed and/or tapped to optionally seat push rod 352 to socket 380 screwed into stem 120. Insertion of the stem is aided by vibrations generated by stem vibrator 354 which is controlled by controller 457, optionally based on input provided by a user. It is noted that whereas display 458 and controller 457 are shown as physically part of handheld housing 456 the display and controller may be separate from the housing and be configured to communicate wirelessly with pusher tool 450.

Figure 5:
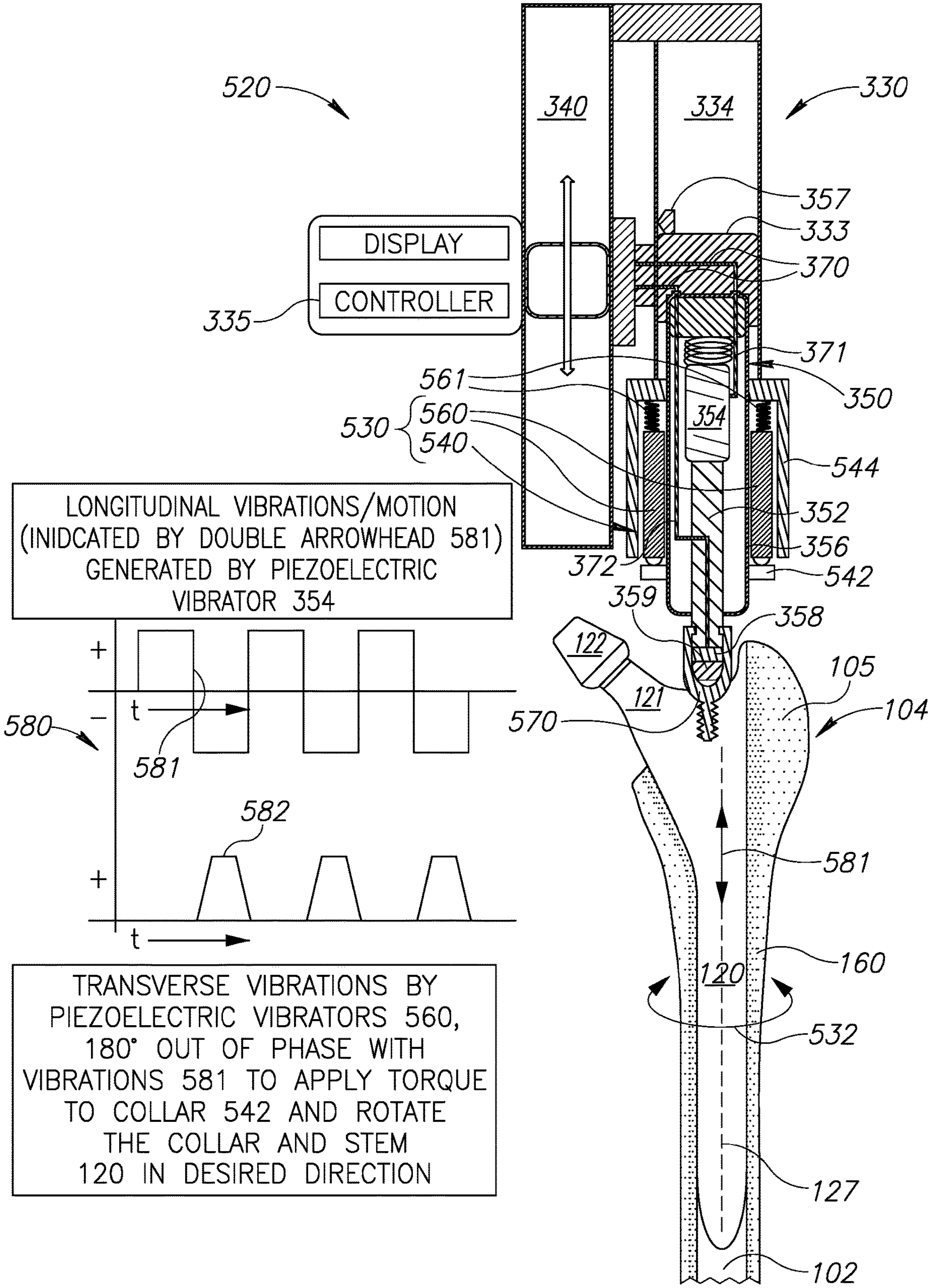
FIG. 5 schematically shows a STEM-FIT comprising a torquing system for rotating a prosthetic stem being inserted to a femoral canal to an advantageous azimuthal angle about a longitudinal axis of the stem, in accordance with an embodiment of the disclosure.

FIG. 5 schematically shows a STEM-FIT 520, optionally similar to STEM-FIT 320 (FIG. 3), and comprising a torquing system 530, in accordance with an embodiment of the disclosure. Torquing system 530, as discussed below, is operable to rotate pusher tool 350 and thereby prosthetic stem 120 selectively clockwise or counterclockwise to an advantageous azimuthal angle about a longitudinal axis, represented by a dashed line 127 of the stem. A curved double headed arrow 532 schematically represents rotation about longitudinal axis 127 clockwise and counterclockwise.

Torquing system 530 optionally comprises a torquing transmission 540 having a rotation collar 542, and a housing 544 attached to guide tube 334. Torquing system 530 optionally comprises two piezoelectric torquing vibrators 560 housed in housing 544. Resilient elements, represented by springs 561, press the torquing vibrators to rotation collar 542. Rotation collar 542 may be an integral part of pusher tool 350. Optionally, rotation collar is rotatably mounted to housing 544 by a suitable bearing (not shown), and couples to pusher tool 350 when the pusher tool is inserted into carriage 333. In an embodiment, controller 335 operates to excite vibrations in torquing vibrators 560 that rotate rotation collar 542 and thereby pusher tool 350 selectively clockwise or counterclockwise. Pusher tool 350 is fixed to stem 120 optionally by a "nose couple" 570 that fixes push rod 352 to the stem and prevents rotation of the push rod relative to the stem.

In an embodiment, to rotate stem 120, controller 335 excites stem vibrator 354 to generate longitudinal vibrations, and torquing vibrators 560 to generate vibrations that are 180° out of phase with the longitudinal vibrations to apply torque to rotation collar 542. Longitudinal vibrations are schematically represented by a double arrowhead arrow 581 along axis 127 of stem 120 and as a function of time t by a train of square pulses in a graph 580. Out of phase vibrations that controller 335 generates in torquing vibrators 560 to apply torque to rotation collar 542 are schematically represented as a function of time tin graph 580 by trapezoidal pulses 582. Pulses 582 are 180° out of phase with longitudinal vibrations 581 so that pulses 582 apply torque to rotate rotation collar 542 and thereby stem 120 during times when longitudinal vibrations 581 translate stem 120 proximally, that is move stem 120 in a direction out from femoral canal 102. The out of phase vibrations facilitate rotation of stem 120 by reducing friction between the stem and femur 102 when torque is applied to rotation collar 542.

In an embodiment a STEM-FIT comprises at least one acoustic sensor configured to be coupled to an external surface region of a portion of a thigh comprising a femur being operated on using the STEM-FIT to insert a stem into the femur. Optionally the at least one sensor comprises a plurality of sensors distributed on the external surface region. In an embodiment the plurality of sensors comprises a bracelet of sensors coupled to and surrounding the surface region. A stem vibrator in the STEM-FIT coupled to the stem may be used to generate vibrations of the stem to couple acoustic waves, which may be referred to as "inside-out" acoustic waves, to the femur that propagate from inside the femur to the surface of the thigh region, where the acoustic waves are sensed by the at least one acoustic sensor. Signals, optionally referred to as inside-out signals generated by the at least one acoustic sensor responsive to the sensed acoustic waves may be processed by a STEM-FIT processor to determine features of the inside-out signals, femoral bone, and/or tissue surrounding femoral bone in which the stem is located, that are indicative of features of coupling of the stem to the femoral bone.

Optionally, the STEM-FIT vibrator is controlled by the STEM-FIT controller to generate ultrasound (US) inside-out waves that couple to the femoral bone and surrounding tissue and propagate from inside the femur to the thigh surface region. In an embodiment, the STEM-FIT processor operates to provide an ultrasound image, an inside-out US image, of a portion of femoral bone, and/or thigh tissue surrounding the portion of femoral bone in which the stem is located. In an embodiment the STEM-FIT processor controls insertion of the stem into the femur based on the inside-out signals and/or an inside out US image.

Figure 6:
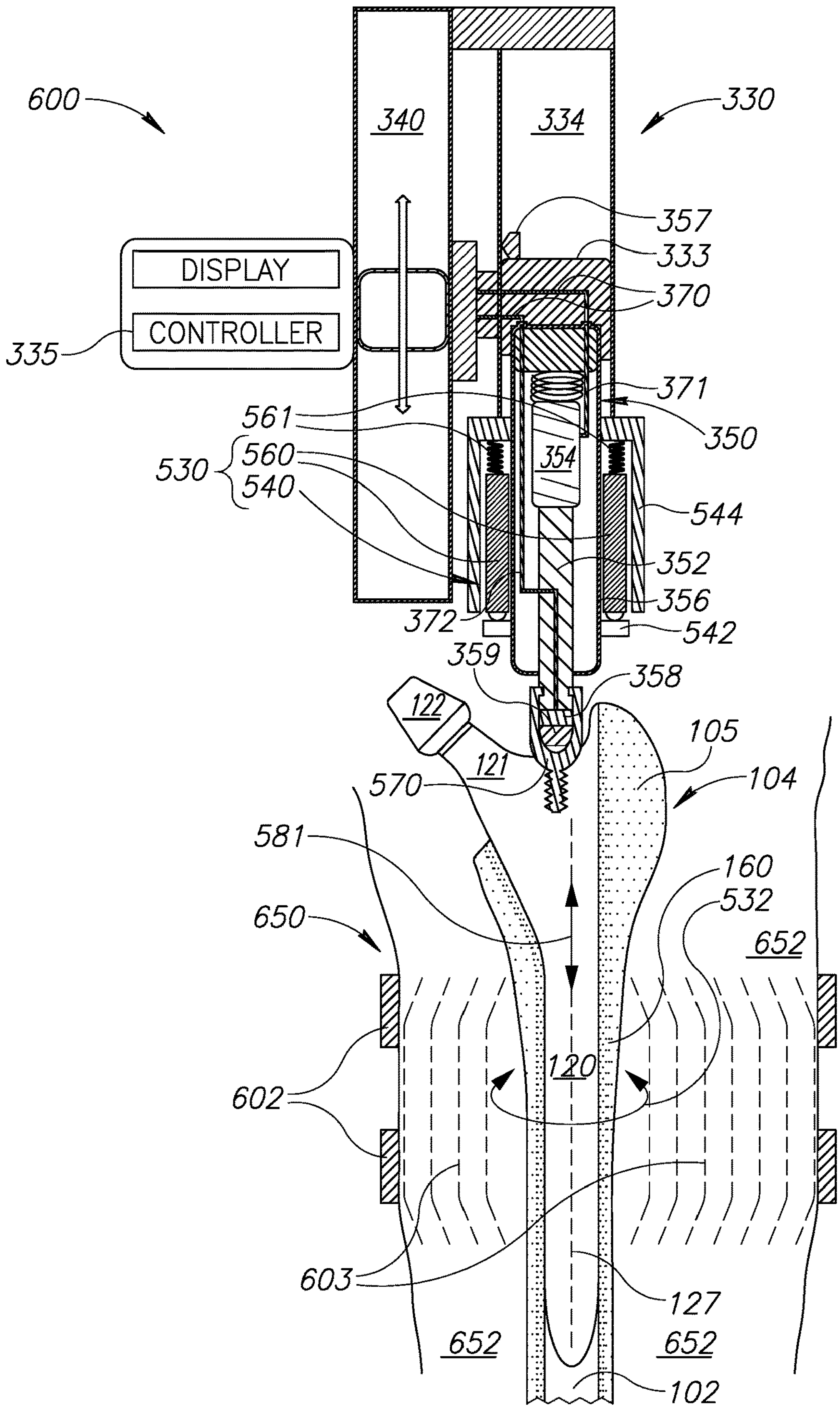
FIG. 6 schematically shows a STEM-FIT operating to insert a stem into a femur and acquire an acoustic image, an "inside-out US image" of tissue in a region of a thigh surrounding a portion of the femur into which the stem is being inserted, in accordance with an embodiment of the disclosure.

FIG. 6 schematically illustrates a STEM-FIT 600, optionally a STEM-FIT similar to STEM-FIT 520 shown in FIG. 5, operating to insert a stem 120 into a femur 104 and acquire an inside-out US image of tissue 652 in a region of a thigh 650 surrounding a portion of femur 104 in which stem 120 is being inserted, in accordance with an embodiment of the disclosure. STEM-FIT 600 comprises, optionally, a plurality of acoustic sensors 602 mounted to thigh 650 operable to sense inside-out acoustic waves, represented by dashed arcs 603, produced by vibrations that the STEM-FIT generates in stem 120. Controller 335 may be configured having computer executable instructions that are executable to process inside-out signals generated by sensors 602 to generate an inside-out US image of the thigh tissue region 652 surrounding stem 120, in accordance with an embodiment of the disclosure.

Figure 7A:
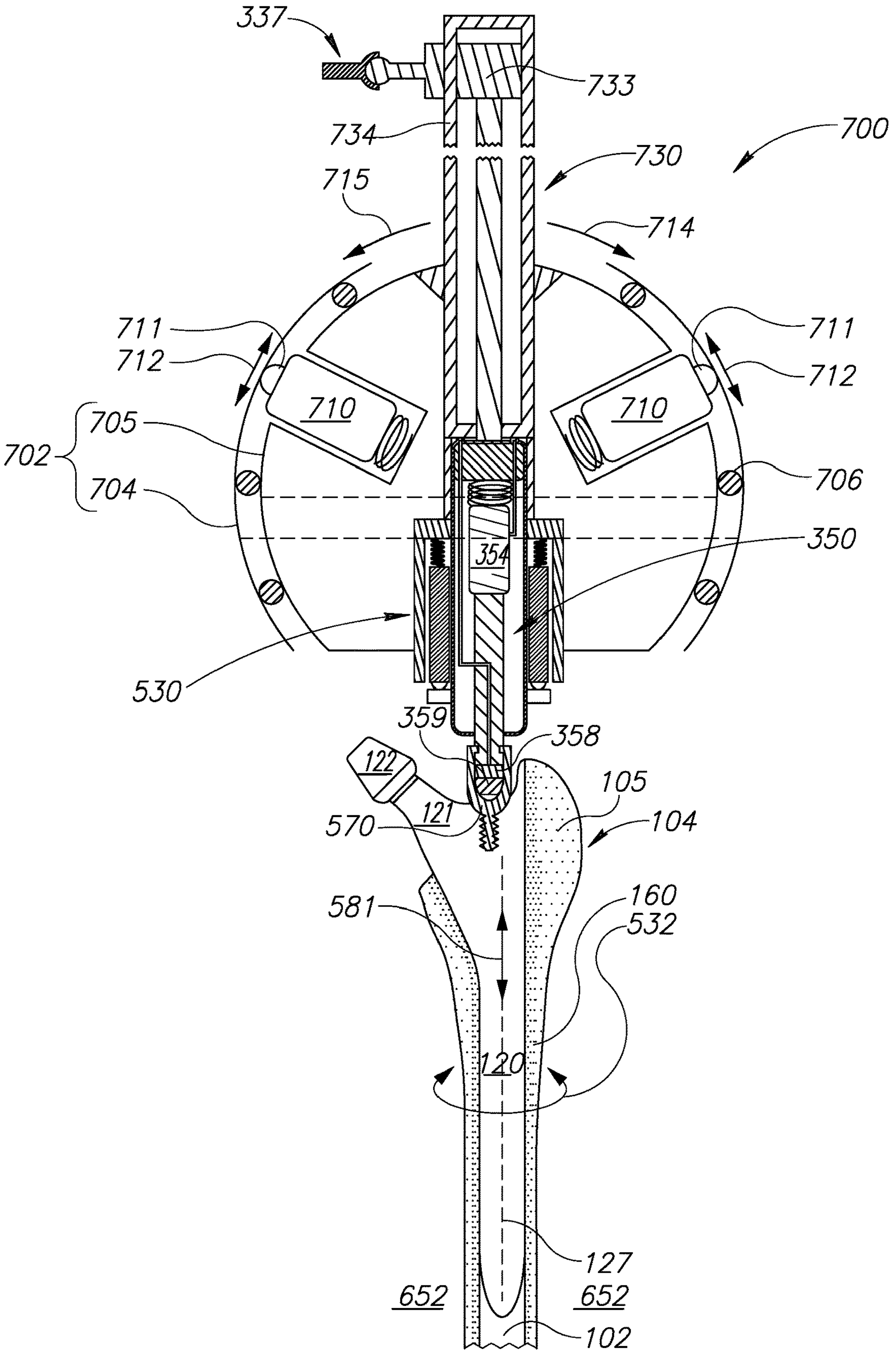
FIGS. 7A and 7B schematically show a STEM-FIT configured to control in real time both an azimuthal angle and/or a polar angle of a stem during insertion of the stem into a femur in accordance with an embodiment of the disclosure.
Figure 7B:
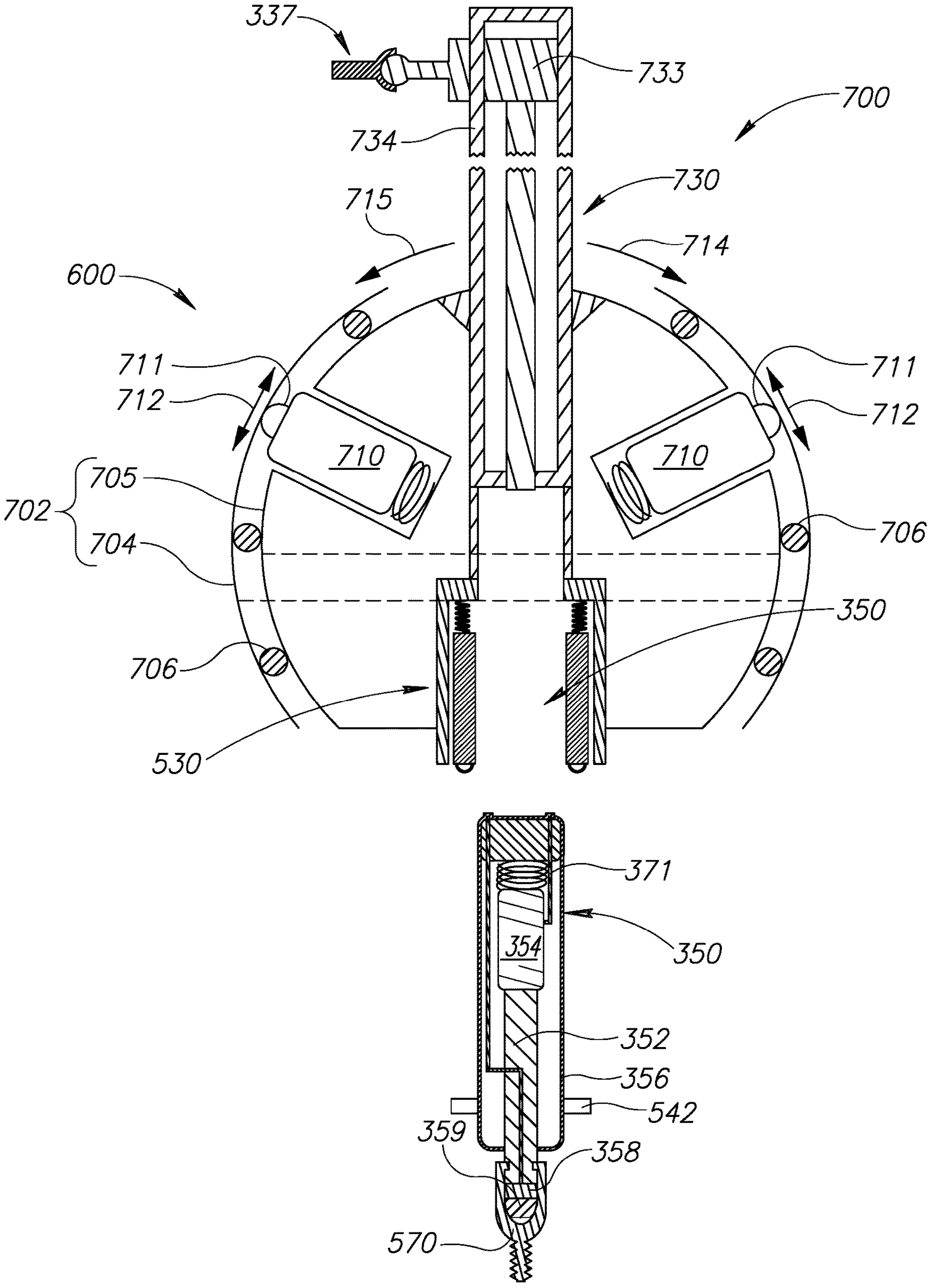

FIG. 7A schematically shows a STEM-FIT 700 comprising a global attitude system (GAS) 702 operating to insert a stem 120 into a femur 104. Stem-fit 700 optionally comprises a driver 730 similar to driver 330 shown in FIGS. 5 and 6 having a throwaway a pusher tool 350 removably mounted to a carriage 733 housed in a guide tube 734. Carriage 733 may be coupled, optionally by a ball and socket joint 735, to a rodless cylinder such as cylinder 340 shown in FIG. 6 that is controllable to control motion of carriage 733 in guide tube 734 and thereby motion of pusher tool 350. FIG. 7B schematically shows an enlarged image of GAS 702 in which pusher tool 350 is schematically shown removed from GAS 702.

GAS 702 optionally comprises an outer shell 704, optionally referred to as a stator, that is shaped as a segment of a sphere, and an inner shell 705, optionally referred to as a rotor, that is nested inside and rotatably coupled to the stator by bearings 706 and at least one piezoelectric motor 710. Driver 730 is fixed to rotor 705 optionally by fixing guide tube 734 to the rotor.

At least one piezoelectric motor 710 is optionally fixed to rotor 705 and comprises a coupling tip 711 that presses onto an inside surface of stator 704. Excitation of the at least one piezoelectric motor 710 to generate vibrations in coupling tip 711 in directions indicted by double arrowhead 712 that are controllable to rotate rotor 705 clockwise or counter clockwise about an axis perpendicular to the plane of FIG. 7, in directions indicated by arrows 714 and 715 respectively. Rotation of rotor 705 in directions other than directions indicated by arrows 714 and 715 may be provided by exciting at least one piezoelectric motor 710 to generate vibrations in coupling tips 711 in directions other than in the plane of FIG. 7. For example, at least one piezoelectric motor 710 may be excited to rotate rotor 705 substantially about any axis through the center of the rotor.

Since driver 730 is fixed to rotor 705, GAS 702 may be controlled to rotate driver 730 and thereby stem 120 fixed to driver 730 about any axis through the center of the rotor. In particular GAS 702 may be controlled to control a polar angle of the driver and stem, and/or an azimuthal angle of the driver and stem, in accordance with an embodiment of the disclosure.

In an embodiment a STEM-FIT apparatus may be configured as a modular tool set comprising a mandrel configured to couple to and transmit vibrations to different tools that may be used to perform for example a hip or knee transplant in accordance with an embodiment of the disclosure.

Figure 8A:
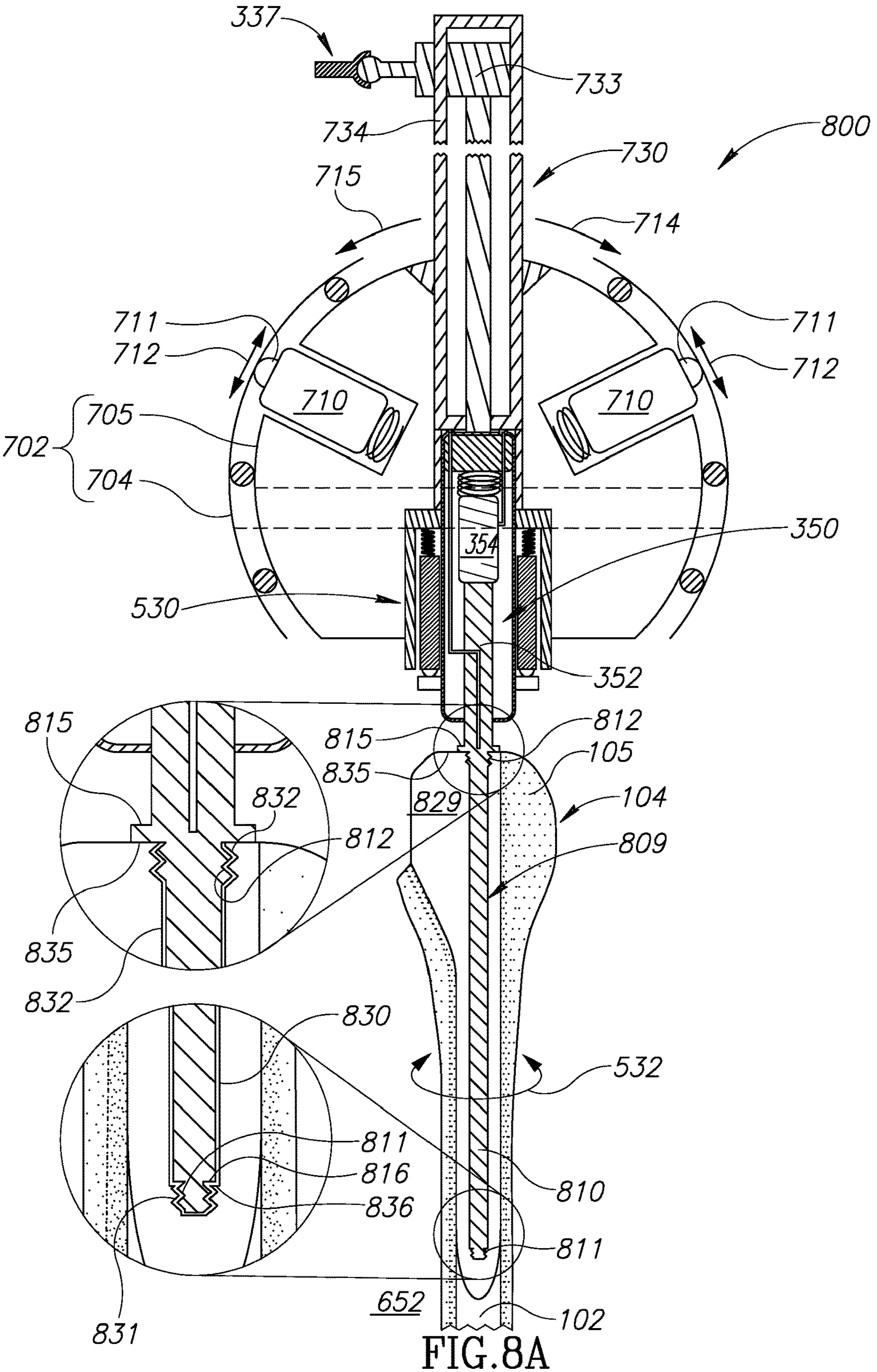
FIG. 8A schematically shows a modular STEM-FIT comprising a mandrel mounted with an exchangeable broaching tool, in accordance with an embodiment of the disclosure.
Figure 8E:
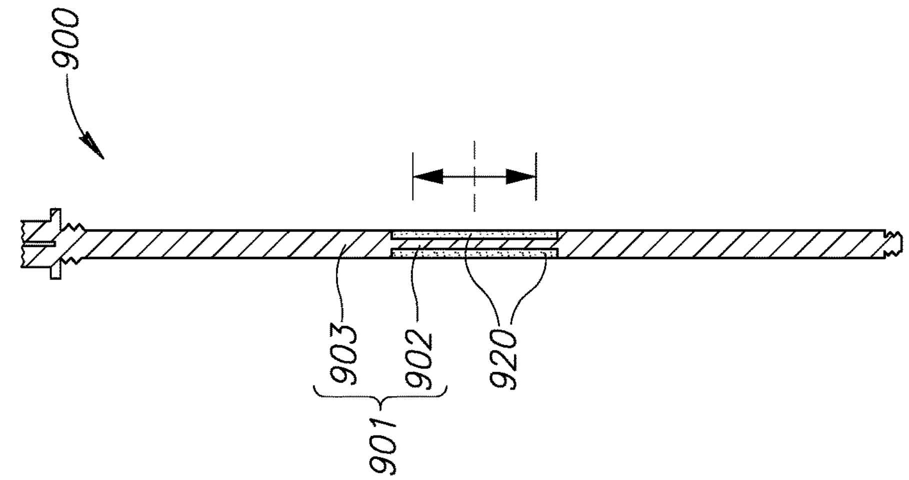
FIGS. 8D-8E schematically show different mandrels, in accordance with an embodiment of the disclosure.
Figure 8D:
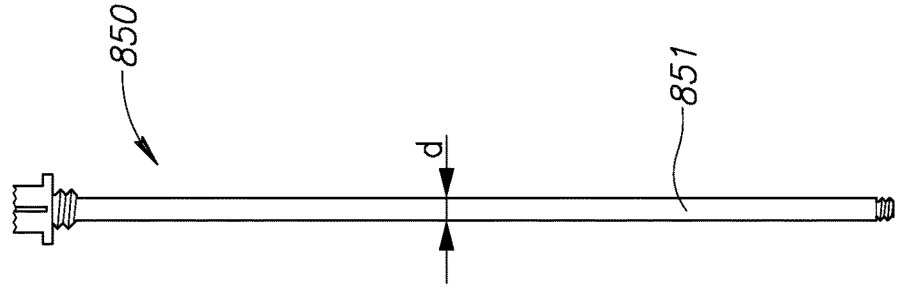

FIG. 8A schematically shows a modular STEM-FIT 800 optionally comprising a mandrel 809, mounted with, by way of example, a broaching tool 829 that is readily detachable from the mandrel to be exchanged for a different tool in accordance with an embodiment of the disclosure. FIG. 8B schematically shows broaching tool 829 dismounted and separate from mandrel 809, which is schematically shown in FIG. 8C.

Mandrel 809 is configured to be coupled to at least one or any combination of more than one of vibrators, actuators, and/or motors that are controllable to impart desired vibrations and movement to the mandrel and thereby to a tool mounted to the mandrel. Whereas FIG. 8A schematically shows mandrel 809 coupled to vibrators and actuators by being integrally formed or connected to pusher rod 350 of STEM-FIT 800, a mandrel in accordance with an embodiment of the disclosure is not limited to being coupled to pusher rod 350. For example, the mandrel may be coupled to a vibrator, actuator, and/or motor, in accordance with any of the configurations shown in the figures and/or described in the description.

Figure 8C:
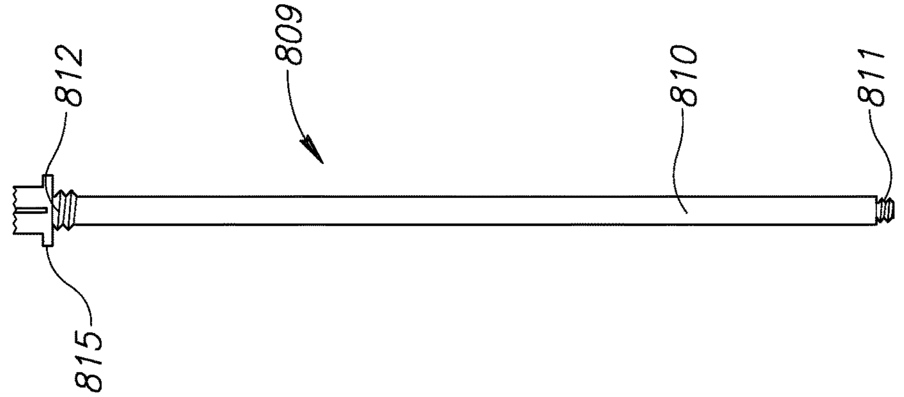
FIG. 8C schematically shows the mandrel shown in FIG. 8A disassembled from the broaching tool, in accordance with an embodiment of the disclosure.
Figure 8B:
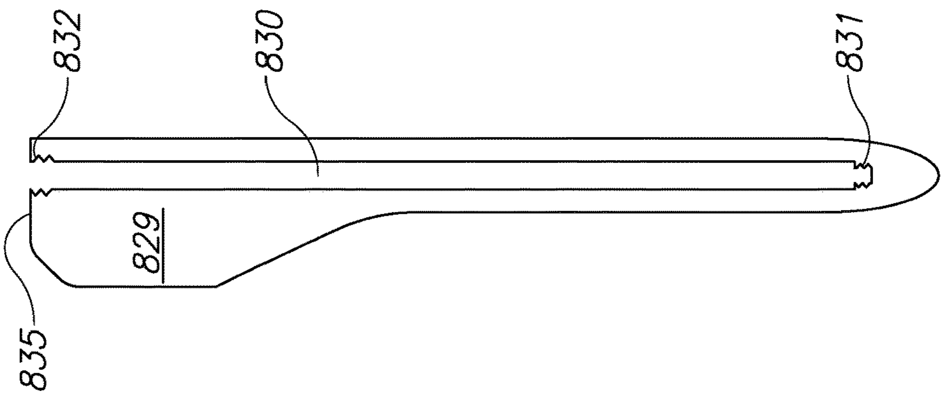
FIG. 8B schematically shows the broaching tool shown in FIG. 8A disassembled from the mandrel in accordance with an embodiment of the disclosure.

In an embodiment as shown in FIGS. 8A-8C, mandrel 809 comprises a circularly cylindrical rod 810 having formed thereon lower and upper sets of threads 811 and 812 respectively. Broaching tool 829 is formed having an, optionally, cylindrical recess 830 (FIG. 8B) dimensioned to receive rod 810 and having lower and upper thread sets 831 and 832 (FIG. 8B) that respectively match lower and upper thread sets 811 and 812 of mandrel 809. Mandrel lower thread set 811 has a smaller major diameter than a major diameter of the mandrel upper thread set 812. The smaller major diameter of the lower thread set facilitates screwing the mandrel into the broaching tool. Optionally, a portion of mandrel rod 810 between thread sets 811 and 812 has a diameter, hereinafter also referred to as a rod diameter, that is substantially uniform throughout its length and substantially the same as an internal diameter, hereinafter also referred to as a recess diameter, of recess 830 between thread sets 831 and 832.

Optionally the matching thread sets comprise a relatively small number of threads. Optionally, the thread sets have three or less than three threads. Optionally mandrel 809 has a collar 815 that seats on a top surface 835 of broaching tool 829 when the broaching tool is completely screwed onto the mandrel. Depth to which mandrel 809 is screwed in to broaching tool 829 may be determined by contact of collar 815 with broach surface 835 and/or contact of a lip 816 at the bottom of bottom threads 811 with a top "shelf" 836 of broaching tool bottom threads 831. In an embodiment once mandrel 809 and broaching tool 829 are properly screwed together, the broaching tool may be firmly held in place by a ratchet lock (not shown) comprising a spring loaded pawl (not shown) optionally formed on top surface 835 of the broaching tool. The broaching tool may be unscrewed from the mandrel after disengaging the pawl.

Whereas broaching tool 829 may be formed from a metal, in an embodiment broaching tools such as broaching tool 829 may be formed by 3D printing of a suitable material or injection molding from a plastic, optionally a high impact plastic. Forming broaching tools from a plastic is facilitated because the broaching tool is inserted into a femur during a hip replacement procedure using vibrations in accordance with an embodiment of the disclosure instead of by hammering with an impactor. As a result, during hip replacement in accordance with an embodiment, a broaching tool is not subject to the mechanical shock of impactor blows to which broaches are subject during conventional hip replacement procedures. It is expected that forming broaching tools by injection molding a plastic will provide for relatively inexpensive broaching tools that may be disposed of after a single use.

Whereas the rod diameter of mandrel 809 shown in FIG. 8A-8C is indicated as being substantially the same as that of recess 830 a mandrel in accordance with an embodiment may have a rod diameter that is different from that of a recess diameter of a recess into which it is inserted. Furthermore the rod diameter may not be the same throughout the length of the rod, nor the rod a straight rod.

FIG. 8D schematically shows a mandrel 850 comprising a rod 851 having a diameter indicated by arrow dimension lines labeled "d" smaller than the diameter of recess 830 into which it is inserted.

In an embodiment to provide vibrations of a mandrel that are conducive to inserting a broaching tool, such as broaching tool 829 or broaching tool 890 (FIG. 8G), into femoral canal 102, the mandrel itself may comprise a piezoelectric vibrator. By way of example FIG. 8E schematically shows a cross section view of a mandrel 900 comprising, optionally one, optionally cylindrical piezoelectric vibrator 920. Mandrel 900 comprises a rod 901 having optionally two large diameter sections 903 separated by a small diameter section 902. Cylindrical piezoelectric vibrator 920 is mounted to the small diameter section. The small diameter section may be a rod having one or both ends threaded to match a thread/s in the large diameter sections. Mandrel 900 may be assembled by screwing the small diameter rod into one of the large diameter sections, mounting piezoelectric vibrator 920 onto the small diameter rod, and then screwing the other large diameter section to the small diameter rod. Optionally, piezoelectric vibrator is excited to generate longitudinal vibrations in the vibrator and thereby in rod 901.

Figure 8G:
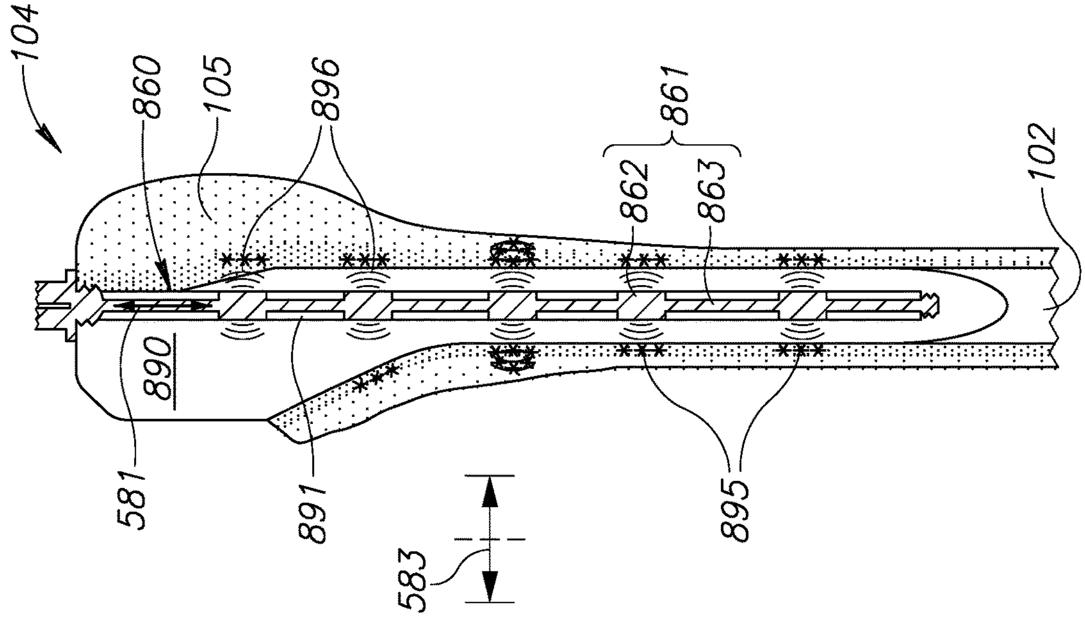
FIG. 8G schematically shows the mandrel shown in FIG. 8F mounted with a broaching tool and operating to deliver a medicament by sonophoresis, in accordance with an embodiment of the disclosure.
Figure 8F:
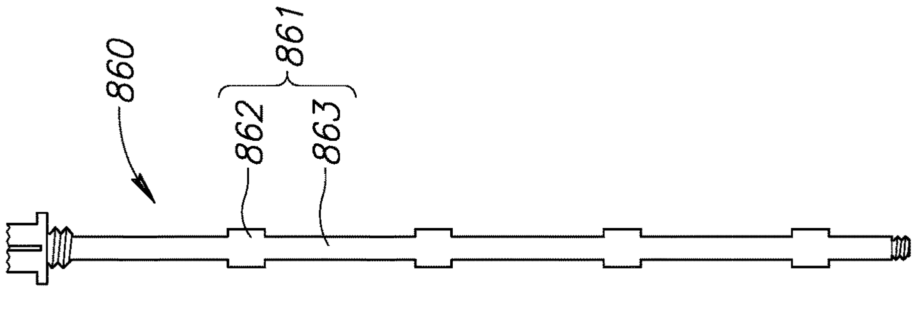
FIG. 8F schematically shows a mandrel configured to generate vibrations advantageous for delivering a medicament by sonophoresis to bone tissue during a hip replacement procedure, in accordance with an embodiment of the disclosure.

FIG. 8F schematically shows a mandrel 860 comprising a rod 861 having a diameter that varies along the length of the rod in accordance with an embodiment of the disclosure. Optionally as shown in the figure rod 861 has relatively large diameter sections 862, also referred to as rings 862, separated by relatively small diameter sections 863 also referred to as spindles 863. Acoustic impedance of rod 861 changes abruptly at boundaries between rings 862 and spindles 863. As a consequence of the change in acoustic impedance, a portion of energy in longitudinal vibrations excited to propagate along rod 861 is converted to transverse vibrations of rings 862 which act as acoustic horns to propagate acoustic energy along directions away from and perpendicular to rod 861. As described below with respect to FIG. 8G, the conversion of longitudinal vibrational energy to transverse vibrational energy of rings 862 may be used to deliver a medicament by a sonophoresis effect to internal bone tissue during a hip transplant operation.

FIG. 8G schematically shows mandrel 860 mounted to a broaching tool 890 by insertion of the mandrel into a recess 891 of the broaching tool in accordance with an embodiment. Optionally, recess 891 is dimensioned so that the surface of rings 862 of the mandrel are in close contact with the wall of recess 891. Optionally, a layer of a suitable acoustic coupling fluid (ACF) is introduced and trapped between the surfaces of rings 862 and wall of recess 891. In an embodiment a medicament schematically represented by asterisks 895 is deposited and adhered to surface regions of broaching tool 890 that are substantially located opposite to rings 862. Optionally, the surface regions are formed having dimples in which the medicament is deposited. The broaching tool is schematically shown located in a femoral canal 102 of a femur 104 of a patient undergoing a hip replacement.

In accordance with an embodiment, longitudinal, optionally ultrasound vibrations schematically represented by a double arrowhead arrow 581 are excited to propagate in mandrel 860 along rod 861 and generate transverse ultrasonic vibrations schematically represented by a double arrowhead arrow 583 in rings 862. The rings, acting as ultrasonic horns, transmit ultrasonic vibrations, schematically represented by arcs 896 into broaching tool 890. The ultrasonic vibrations release medicament 895 from surface regions of broaching tool 829 in which the medicament is deposited and deliver the medicament by sonophoresis to regions of trabecular bone 105 surrounding broaching tool 890.

It is noted that whereas rings 862 in mandrel 860 are used to generate sonophoresis sound waves to deliver a medicament, the rings are passive ultrasonic horns in the sense that they generate the sonophoresis vibrations because of the change in thickness relative to spindles 863 in the mandrel. Optionally, a mandrel used for sonophoretic delivery of medicaments in accordance with an embodiment may comprise active ultrasonic horns, such as piezoelectric vibrators mounted to the mandrel, to provide sonophoretic delivery of medicaments. For example, piezoelectric vibrator 920 comprised in mandrel 900 (FIG. 8E) may be excited to vibrate transversally to generate sonophoretic acoustic waves, or rings 862 of mandrel 860 may be replaced by piezoelectric vibrators for use as active ultrasonic horns.

It is noted that whereas vibrator 920 is described as generating sonophoretic acoustic waves, in an embodiment the vibrator may be used to generate and sense ultrasonic waves that are reflected from interfaces between a broaching tool mounted to mandrel 900 and bone of a femur into which the mandrel and broaching tool are introduced. The reflected waves may be used to provide ultrasound images of the interfaces and coupling of the broaching tool to the bone.

Figure 9A:
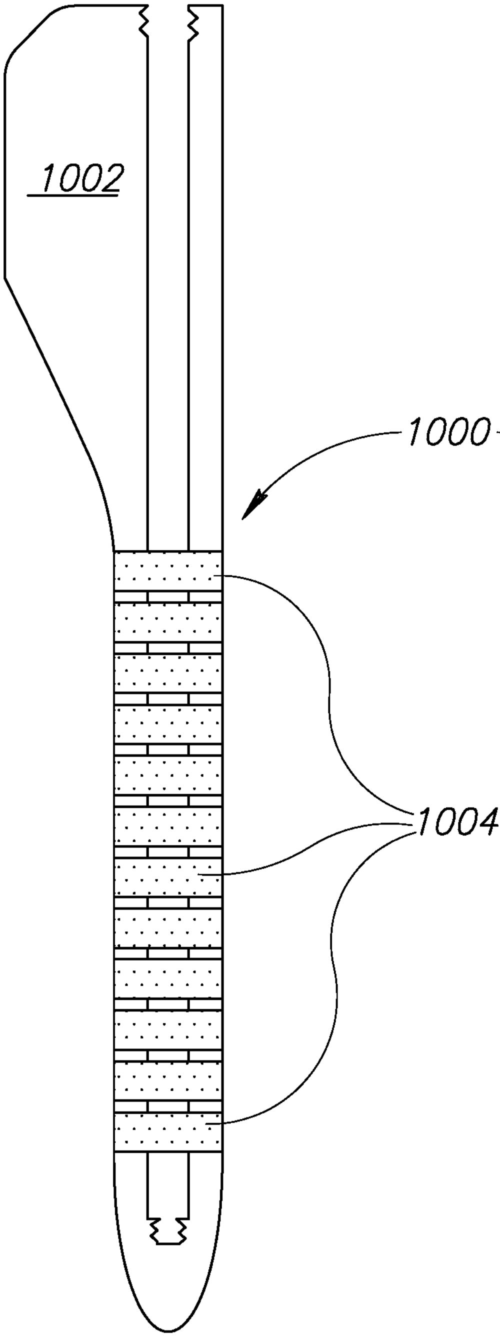
FIGS. 9A and 9B schematically illustrate a broaching tool comprising shape memory alloy expansion braces operable during a hip replacement procedure to compress trabecular bone in a femoral canal to a desired shape in preparation of the femur for receiving a prosthetic stem, in accordance with an embodiment of the disclosure.
Figure 9B:
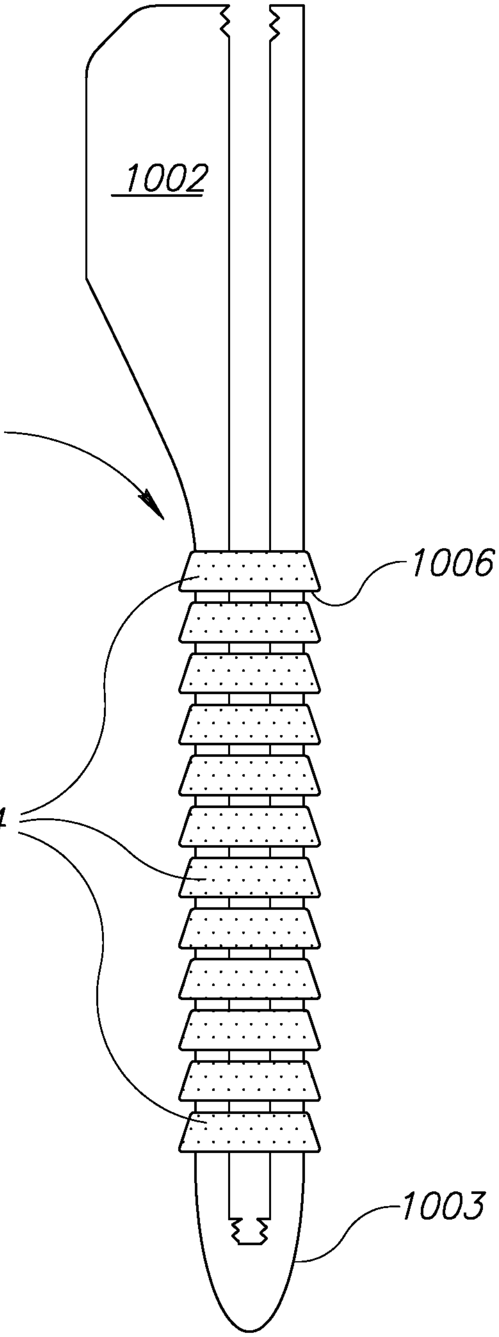

Generally a plurality of between four and seven broaches are inserted by hammering into a femoral canal to prepare a femoral canal for receiving a permanent prosthetic stem to which a prosthetic hip joint ball is mounted. FIGS. 9A and 9B schematically shows a STEM-FIT broaching tool 1000 that may be used in place of a plurality of broaches and by itself optionally used with only a single insertion to prepare a femur for insertion of final prosthetic stem in accordance with an embodiment of the disclosure.

Broaching tool 1000, hereinafter also referred to as an All-in-One broach or simply an All-in One, is optionally configured to be mounted to a mandrel in accordance with an embodiment of the disclosure. Broaching tool 1000 optionally comprises a base broach 1002 that supports a plurality of shape memory expansion braces 1004 seated in matching recesses (not shown). All-in-One 1000 has a delivery configuration schematically shown in FIG. 9A and a deployed configuration schematically shown in FIG. 9B.

In the delivery configuration prior to insertion into a femoral canal shown in FIG. 9A, expansion braces 1004 of All-in-One 1000 are in a relatively cold temperature, martensite state and, optionally, the expansion braces conform to and do not substantially protrude out from the base broach. After insertion into a femoral canal, body temperature, and/or an active heating device (not shown) such as a heating coil and/or a hot water circulation tube (not shown) which may be provided in a mandrel to which All-in-One is mounted, increases the temperature of expansion braces 1004. The temperature increase causes All-in-One 1000 to transition to the deployed state shown in FIG. 9B, in which the expansion braces convert to an austenite state. In converting to the austenite state the expansion braces expand to protrude out from the base broach and compress and form trabecular bone in the canal to a shape suitable for receiving a prosthetic stem. Optionally in transitioning to the austenite state the expansion braces expand to a conical frustum or segment of a sphere with a larger end 1006 of the frustrum or segment facing a distal end 1003 of the All-in-One.

Whereas shape memory expansion braces have been described as parts of an All-in-One broach, shape memory expansion braces of various shapes may be comprised in a final stem prosthesis mounted to a femur to aid in preventing loosening of the stem after insertion. For example, a stem having expansion braces similar to expansion braces 1004 may be configured to expand to aid in anchoring the stem to a femur after insertion into the femoral canal.

It is noted that in the figures and discussion of mandrels the mandrels have been shown as extending substantially the full length of stems that are configured to be mounted to the mandrel. However, mandrels in accordance with an embodiment of the disclosure are not limited to "full-length" mandrels and may have any length advantageous to the applications for which they are intended to be used. A mandrel by way of example may be relative short and extend only a small fraction of the length of a mandrel.

It is noted that whereas STEM-FIT has been described for use in a hip replacement procedure embodiments of the disclosure are not limited to hip replacement procedure. For example, a STEM-FIT in accordance with an embodiment of the disclosure may be used to insert a stem into a femoral canal during a knee replacement procedure or used to insert a stem into a humeral medullary canal during a shoulder replacement procedure.

There is therefore provided in accordance with an embodiment of the disclosure an apparatus for performing a joint replacement procedure, the apparatus comprising: a vibrator configured to be coupled to a stem and be excited to generate vibrations in the stem during a joint replacement operation to insert the stem into and/or to extract the stem out from a bone canal, the stem having a longitudinal axis; a driver operable to apply force to the stem; and a controller operable to control the vibrator and the driver to respectively generate vibrations in and apply force to the stem that cooperate to insert the stem into or extract the stem out from the canal. Optionally, the vibrations comprise longitudinal vibrations that are substantially parallel to the longitudinal axis of the stem.

Additionally or alternatively, the vibrations may comprise transverse vibrations that are substantially perpendicular to the longitudinal axis of the stem. In an embodiment, the force comprises a continuous force. In an embodiment, the force comprises an impulse force.

In an embodiment, the controller controls the vibrator and the driver to simultaneously generate vibrations in the stem and apply the force to the stem. In an embodiment, the controller controls the vibrator and the driver to non-simultaneously respectively generate vibrations in the stem and apply the force to the stem. In an embodiment, the vibrator comprises at least one piezoelectric vibrator that the controller controls to generate the vibrations.

In an embodiment the apparatus comprises a torquing system controllable by the controller to apply torque to rotate the stem when in the canal to a desired azimuthal angle about the longitudinal axis of the stem during insertion and/or extraction of the stem from the canal. Optionally, the controller controls the vibrator and the driver selectively to simultaneously or to non-simultaneously respectively generate vibrations in the stem and apply torque to the stem.

In an embodiment the apparatus comprises an attitude control system controllable by the controller to control a direction along which the longitudinal axis of the stem points during insertion and/or extraction of the stem from the canal. Optionally, the controller controls the vibrator and the attitude control system selectively to simultaneously or to non-simultaneously respectively generate vibrations in the stem and to control a direction along which the longitudinal axis of the stem points.

In an embodiment the apparatus comprises at least one vibration sensor that generates and transmits vibration sensor signals to the controller responsive to vibrations excited in the stem by the vibrator during a time period when the stem is in the femoral cavity. Optionally, the vibration sensor signals that the at least one vibration sensor transmits comprise sensor signals generated responsive to vibrations exhibited by the stem while the controller controls the vibrator to generate vibrations in the stem.

Additionally or alternatively, the sensor signals that the at least one sensor transmits comprise sensor signals generated responsive to vibrations exhibited by the stem while the controller prevents the vibrator from generating vibrations in the stem. Additionally or alternatively, the controller processes the vibration sensor signals to determine at least one characteristic of the vibrations. Optionally, the at least one characteristic comprises a feature of a frequency spectrum of the vibrations. Additionally or alternatively, the at least one characteristic comprises at least one resonant frequency of the stem in the canal. In an embodiment the controller controls at least one or any combination of more than one of the vibrator, the driver, the torquing system, and/or the attitude control system responsive to the at least one characteristic.

In an embodiment the apparatus comprises at least one force sensor that generates and transmits force sensor signals to the controller responsive to force applied to the stem when the stem is in the femoral cavity. Optionally, the controller controls at least one or any combination of more than one of the vibrator, the driver, the torquing system, and/or the attitude control system responsive to the force sensor signals.

In an embodiment the apparatus comprises a mandrel to which the stem is mountable. Optionally, the mandrel comprises a piezoelectric motor controllable by the controller to generate vibrations in the mandrel and thereby in the stem.

In an embodiment the stem is a broach. In an embodiment the stem is a permanent prosthetic stem that that is meant to remain permanently inserted into the bone canal at the conclusion of the procedure. In an embodiment the joint replacement procedure is a hip replacement procedure, a knee replacement procedure, or a shoulder replacement procedure.

There is further provided in accordance with an embodiment a stem for insertion into a bone canal during a joint replacement procedure, the stem comprising: a stem base shaped for insertion into a bone canal during a joint replacement procedure; and a shape memory expansion brace mounted to the stem base and having a contracted delivery configuration and an expanded deployed configuration; wherein the stem is inserted into the canal when the expansion brace is in the delivery configuration and following insertion the brace transitions or is caused to transition to the deployed state.

In an embodiment the stem is a broach and the expansion brace expands to a predetermined deployed state to shape the inside of the canal for receiving a permanent prosthetic stem. In an embodiment the stem is a permanent prosthetic stem and the expansion brace expands to a predetermined deployed state to aid in anchoring the stem to the bone.

In the application, unless otherwise stated, adjectives such as "substantially" and "about" modifying a condition or relationship characteristic of a feature or features of an embodiment of the disclosure, are to be understood to mean that the condition or characteristic is defined to within tolerances that are acceptable for operation of the embodiment for an application for which it is intended. Wherever a general term in the disclosure is illustrated by reference to an example instance or a list of example instances, the instance or instances referred to, are by way of non-limiting example instances of the general term, and the general term is not intended to be limited to the specific example instance or instances referred to. Unless otherwise indicated, the word "or" in the description and claims is considered to be the inclusive "or" rather than the exclusive or, and indicates at least one of, or any combination of more than one of items it conjoins.

Descriptions of embodiments of the disclosure are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims as follows.

The invention claimed is:

1. Apparatus for performing a joint replacement procedure, the apparatus comprising:

a vibrator configured to be coupled to a stem and be excited to generate vibrations in the stem during a joint replacement operation to insert the stem into and/or to extract the stem out from a bone canal, the stem having a longitudinal axis;

a driver operable to apply force to the stem;

a torquing system controllable to apply torque to rotate the stem when in the canal to a desired azimuthal angle about the longitudinal axis of the stem during insertion and/or extraction of the stem from the canal; and a controller operable to control the vibrator, the torquing system, and the driver to respectively generate vibrations in and apply force to the stem that cooperate to insert the stem into or extract the stem out from the canal; and to control the torquing system to rotate and position the stem to an advantageous azimuthal angle.

2. The apparatus according to claim 1 wherein the vibrations comprise longitudinal vibrations that are substantially parallel to the longitudinal axis of the stem.

3. The apparatus according to claim 1 wherein the vibrations comprise transverse vibrations that are substantially perpendicular to the longitudinal axis of the stem.

4. The apparatus according to claim 1 wherein the force comprises a continuous force.

5. The apparatus according to claim 1 wherein the controller controls the vibrator and the driver to simultaneously generate vibrations in the stem and apply the force to the stem.

6. The apparatus according to claim 1 wherein the controller controls the vibrator and the driver to non-simultaneously respectively generate vibrations in the stem and apply the force to the stem.

7. The apparatus according to claim 1 wherein the controller controls the vibrator and the driver selectively to simultaneously or to non-simultaneously respectively generate vibrations in the stem and apply torque to the stem.

8. The apparatus according to claim 1 comprising an attitude control system controllable by the controller to control a direction along which the longitudinal axis of the stem points during insertion and/or extraction of the stem from the canal.

9. The apparatus according to claim 1 wherein the controller controls the vibrator and the attitude control system selectively to simultaneously or to non-simultaneously respectively generate vibrations in the stem and to control a direction along which the longitudinal axis of the stem points.

10. The apparatus according to claim 1 and comprising at least one vibration sensor that generates and transmits vibration sensor signals to the controller responsive to vibrations excited in the stem by the vibrator during a time period when the stem is in the femoral cavity.

11. The apparatus according to claim 10 wherein the vibration sensor signals that the at least one vibration sensor transmits comprise sensor signals generated responsive to vibrations exhibited by the stem while the controller controls the vibrator to generate vibrations in the stem.

12. The apparatus according to claim 10 wherein the sensor signals that the at least one sensor transmits comprise sensor signals generated responsive to vibrations exhibited by the stem while the controller prevents the vibrator from generating vibrations in the stem.

13. The apparatus according to claim 10 wherein the controller processes the vibration sensor signals to determine at least one characteristic of the vibrations.

14. The apparatus according to claim 13 wherein the at least one characteristic comprises a feature of a frequency spectrum of the vibrations.

15. The apparatus according to claim 13 wherein the at least one characteristic comprises at least one resonant frequency of the stem in the canal.

16. The apparatus according to claim 13 wherein the controller controls at least one or any combination of more than one of the vibrator, the driver, the torquing system, and/or the attitude control system responsive to the at least one characteristic.

17. The apparatus according to claim 1 and comprising at least one force sensor that generates and transmits force sensor signals to the controller responsive to force applied to the stem when the stem is in the femoral cavity.

18. The apparatus according to claim 17 wherein the controller controls at least one or any combination of more than one of the vibrator, the driver, the torquing system, and/or the attitude control system responsive to the force sensor signals.

19. The apparatus according to claim 1 and comprising a mandrel to which the stem is mountable the mandrel configured to generate sonophoresis sound waves to deliver a medicament and wherein the stem is configured to have the medicament on a surface of the stem.

20. The apparatus according to claim 1 wherein the stem is a broach or a permanent prosthetic stem.

21. The apparatus according to claim 1 wherein the azimuthal angle is advantageous for matching a prosthetic femoral head that seats on the stem to an acetabular cup mounted in the pelvis to receive the femoral head.

* * * * *